United States Patent [19]
Krause et al.

[11] Patent Number: 5,322,505
[45] Date of Patent: Jun. 21, 1994

[54] SURGICAL INSTRUMENT
[75] Inventors: Kenneth W. Krause, Sandown, N.H.; Richard Crowell, Newbury; Philip B. Sample, Haverhill, both of Mass.
[73] Assignee: Smith & Nephew Dyonics, Inc., Mass.
[21] Appl. No.: 921,563
[22] Filed: Jul. 29, 1992

Related U.S. Application Data

[63] Continuation of Ser. No. 634,599, Dec. 27, 1990, Pat. No. 5,152,744, which is a continuation-in-part of Ser. No. 477,223, Feb. 7, 1990, abandoned.

[30] Foreign Application Priority Data

Oct. 11, 1991 [DE] Fed. Rep. of Germany ....... 4133696
Mar. 10, 1992 [DE] Fed. Rep. of Germany ....... 4207557

[51] Int. Cl.$^5$ ............................................. A61B 17/22
[52] U.S. Cl. ..................... 604/24; 606/170; 606/180
[58] Field of Search ............... 606/167, 170, 171, 180; 128/750-757; 604/22

[56] References Cited

U.S. PATENT DOCUMENTS

| | | |
|---|---|---|
| 745,722 | 12/1903 | Freeman . |
| 1,630,239 | 5/1924 | Binkley et al. . |
| 1,636,636 | 7/1927 | Humble . |
| 2,878,809 | 3/1959 | Treace . |
| 3,618,611 | 12/1971 | Urban . |
| 3,847,154 | 11/1974 | Nordin . |
| 4,020,847 | 5/1977 | Clark, III . |
| 4,167,943 | 9/1979 | Banko . |
| 4,167,944 | 9/1979 | Banko . |
| 4,203,444 | 7/1987 | Bonnell et al. . |
| 4,246,902 | 1/1981 | Martinez . |
| 4,265,231 | 5/1981 | Scheller, Jr. et al. . |
| 4,274,414 | 6/1981 | Johnson et al. . |
| 4,320,761 | 3/1982 | Haddad . |
| 4,445,509 | 5/1984 | Auth . |
| 4,466,429 | 8/1984 | Loscher et al. . |
| 4,512,344 | 4/1985 | Barber . |
| 4,517,977 | 3/1985 | Frost . |
| 4,522,206 | 6/1985 | Whipple et al. . |
| 4,541,423 | 9/1985 | Barber . |
| 4,576,772 | 3/1986 | Carpenter . |
| 4,589,412 | 5/1986 | Kensey . |
| 4,631,052 | 12/1986 | Kensey . |
| 4,646,738 | 3/1987 | Trott . |
| 4,649,919 | 3/1987 | Thimsen . |
| 4,662,371 | 5/1987 | Whipple et al. . |
| 4,681,106 | 7/1987 | Kensey . |
| 4,690,140 | 9/1987 | Mecca . |
| 4,696,667 | 9/1987 | Masch . |
| 4,705,038 | 11/1987 | Sjostrom et al. . |
| 4,738,256 | 4/1988 | Freeman . |
| 4,739,762 | 4/1988 | Palmaz . |
| 4,834,729 | 5/1989 | Sjostrom . |
| 4,842,578 | 6/1989 | Johnson et al. . |
| 4,858,897 | 8/1989 | Irifune . |
| 4,867,155 | 9/1989 | Isaacson . |
| 4,998,527 | 3/1991 | Meyer . |

FOREIGN PATENT DOCUMENTS

| | | |
|---|---|---|
| 0393834 | 10/1990 | European Pat. Off. . |
| 3219629A1 | 12/1983 | Fed. Rep. of Germany . |
| 3828478 | 5/1989 | Fed. Rep. of Germany . |
| 61-265133 | 11/1986 | Japan . |
| 1235321 | 1/1968 | United Kingdom . |

OTHER PUBLICATIONS

Palmaz et al., "Atherosclerotic Rabbit Aortas: Expandable Intraluminal Grafting!" Departments of Radiology, vol. 160, pp. 723-726 (1986).

*Primary Examiner*—Stephen C. Pellegrino
*Assistant Examiner*—William W. Lewis
*Attorney, Agent, or Firm*—Fish & Richardson

[57] ABSTRACT

A surgical instrument that includes a rigid outer member within which is disposed a hollow inner member having rigid proximal and distal ends and a region disposed between the rigid proximal and distal ends that is relieved to render such region relatively flexible. The flexible region is integral with a portion of the proximal end disposed adjacent to the flexible region. The inner member transmits force (such as torsion) applied to its proximal end to move a cutting implement disposed at its distal end and cause it to cut tissue admitted through an opening in the distal region of the outer member. In another aspect, a region of the inner member is weakened (e.g., by relieving an integral region of the member) with respect to the remainder of the inner member to cause this region to break if the force (e.g., torque) applied to the inner member exceeds a predetermined threshold. In yet another aspect, the flexible region is relieved by forming openings therein, and pliable material (such as silicone rubber) is disposed in the openings.

47 Claims, 7 Drawing Sheets

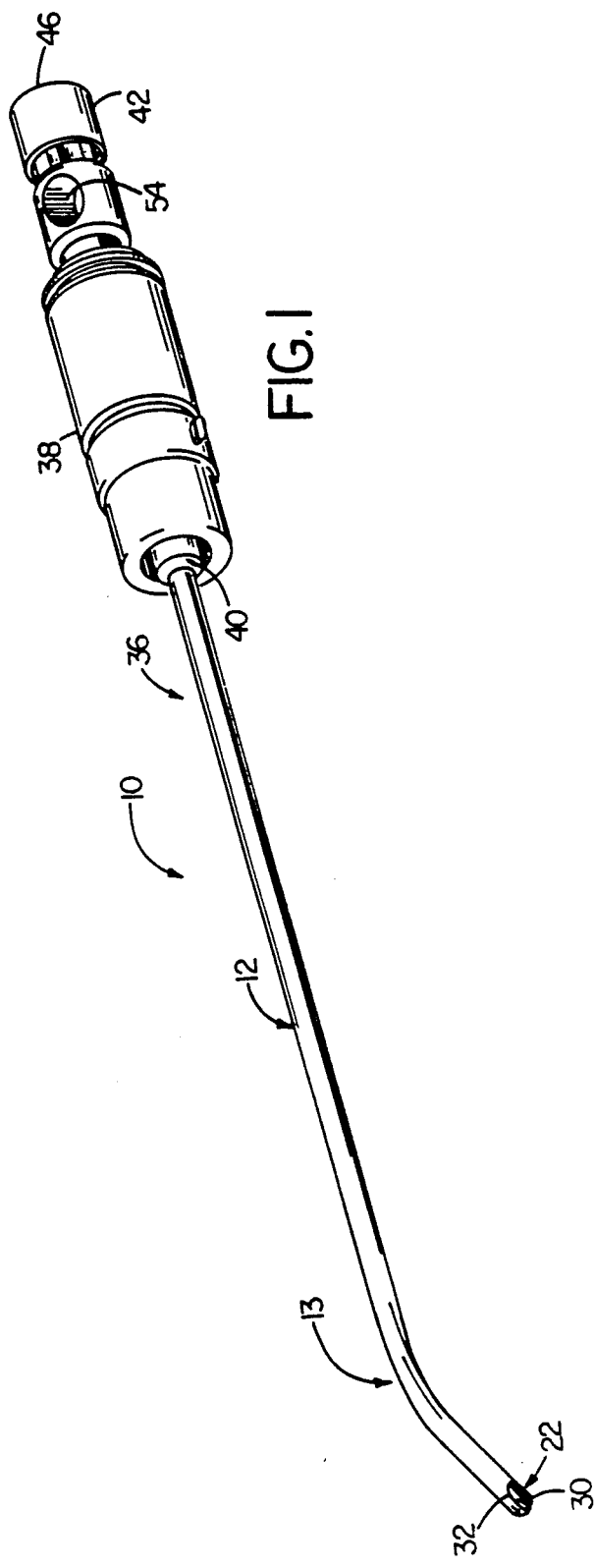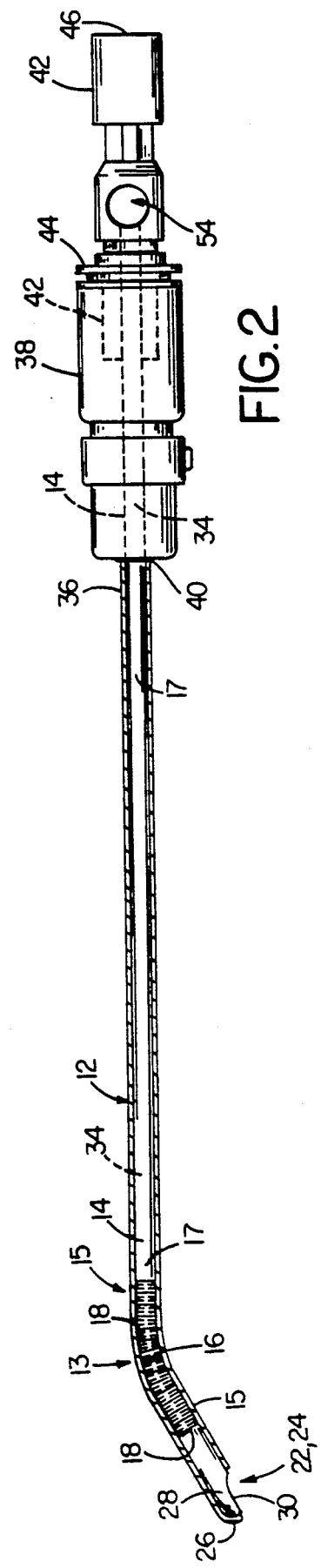

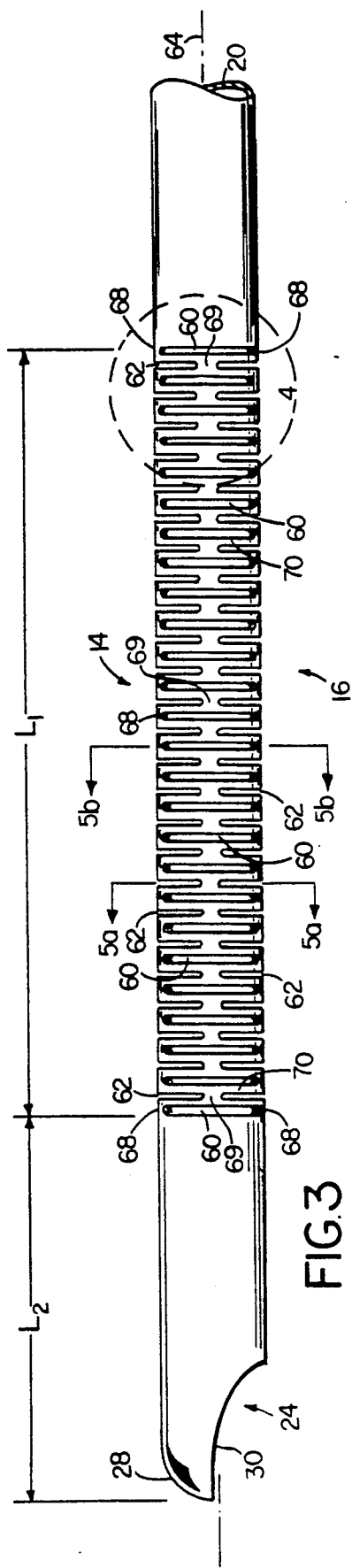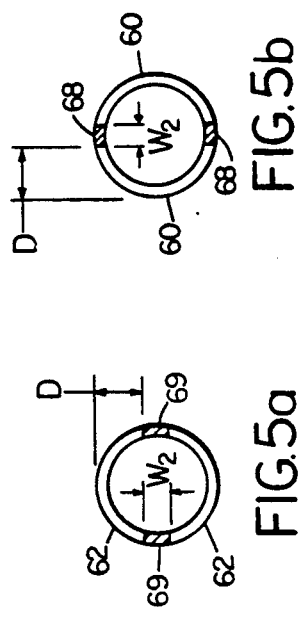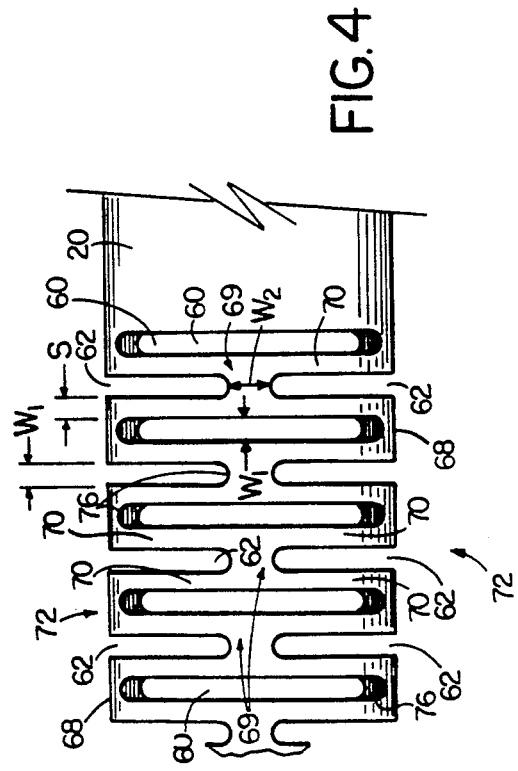

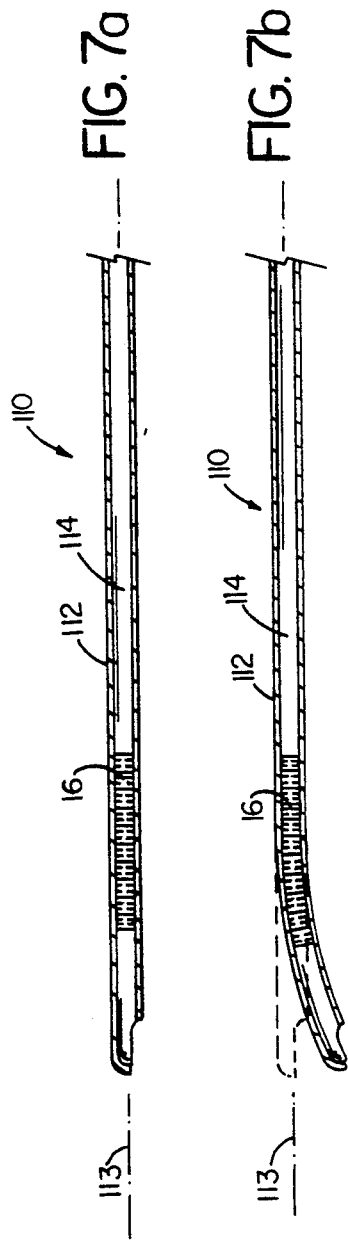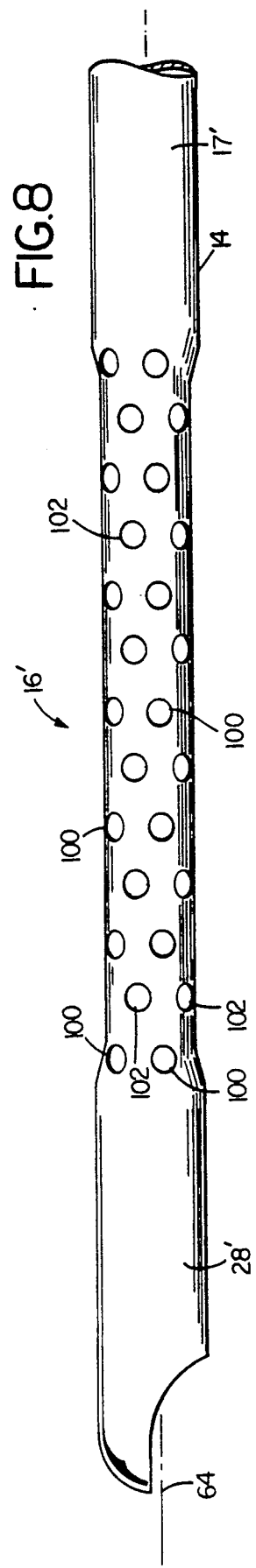

SURGICAL INSTRUMENT

This is a continuation of copending application Ser. No. 07/634,599, filed Dec. 27, 1990, now U.S. Pat. No. 5,152,744, which is a continuation-in-part of Ser. No. 07/477,223, filed Feb. 7, 1990, now abandoned.

BACKGROUND OF THE INVENTION

This invention relates to surgical instruments, and in particular to powered arthroscopic surgical instruments.

Arthroscopic surgical instruments typically include an rigid outer tube within which a rigid inner tube is rotated by a motor. A cutting implement, such as a blade or abrading burr, is disposed on the distal end of the inner tube. Tissue or bone is exposed to the cutting implement through an opening in the distal end of the outer tube, and tissue or bone fragments cut by the rotating blade or burr are drawn through the interior of the inner tube along with irrigating fluid by the use of suction applied at the proximal end of the instrument. Examples of such surgical instruments are described in U.S. Pat. Nos. 4,203,444, 4,274,414, 4,834,729, and 4,842,578, all of which are assigned to the present assignee.

In some instruments, the cutting implement is a hinged jaw mounted on the outer tube near its distal end, and is actuated by the rotating inner tube to pivot on the hinges and cut tissue. Examples of these surgical instruments are described in U.S. Pat. Nos. 4,522,206, 4,662,371, both of which are assigned to the present assignee.

Typical arthroscopic surgical instruments are linear, that is, straight between their proximal and distal ends. It is sometimes useful for such instruments to be curved to facilitate positioning the cutting implement against tissue to be cut without requiring that the instrument be removed from the body and reinserted through an additional puncture. A region of the inner tube is flexible to enable the inner tube to accept the curvature imposed by the outer tube while transmitting the torsion applied by the motor to the blade.

In Trott, U.S. Pat. No. 4,646,738, the inner tube is made flexible with a separate flexible section made from a series of coaxial, spiral layers wound in opposition. The cutting blade is welded to the distal end of the counter-wound helical coils, and the rigid proximal end of the inner tube is secured to the other end of the flexible structure. During operation, torque generated by rotation of the motor in one direction is transmitted to the blade by the tightening of the coil or coils that are wound in that direction, which also serves to counteract the tendency of the oppositely wound coils to be unwound by the rotation.

SUMMARY OF THE INVENTION

One general aspect of the invention is a surgical instrument that includes a hollow inner member having rigid proximal and distal ends disposed for movement within a rigid outer member and which includes a region between its proximal and distal ends that is relieved to render the region relatively flexible; the inner member transmits force applied to its proximal end to move a cutting implement disposed at its distal end and causes it to cut tissue admitted through an opening in the distal region of the outer member.

In another general aspect of the invention, the flexible region is integral with a portion of the proximal end disposed adjacent to the flexible region.

The flexible region accepts curvature changes in the outer member while maintaining a high degree of torsional and axial stiffness. Thus, the inner member is highly suitable for use in a curved surgical instrument. The inner member is rotated over a large range of speeds and applied torque (e.g., by a motor that drives the proximal end of the inner member) without the risk of breaking the inner member (due to its flexibility). The torsional stiffness provided by the flexible region promotes good torque response. That is, the flexible region efficiently transmits torque applied by the motor to the cutting implement, thereby maintaining a high degree of cutting efficiency.

The high torque response is a direct result of the integral nature of the flexible region with respect to the remainder of the inner member (particularly with respect to the proximal end of the inner member to which the torque is applied)—the flexible region need not be tightened in some manner (i.e., "preloaded") when torque is applied before transmitting the torque to the cutting implement (as can occur when helical coils are used). Also, because the inner member does not include a relaxing (i.e., unwinding), and hence expanding, helical coil that is counteracted by a tightening, oppositely wound coil, the possibility of the inner member binding within the outer member is reduced.

Preferred embodiments include the following features.

The flexible region is sufficiently long to span the entire curved region and lie partially within the straight portions of the outer member that bound the curved region.

The flexible region is relieved with a plurality of openings disposed in the walls of the inner member and arranged in a symmetrical pattern.

In one embodiment, the openings are a plurality of circumferentially extending slots disposed in a succession of planes perpendicular to the longitudinal axis of the inner member. The planes are uniformly spaced along the length of the flexible region, and the slots in adjacent planes are circumferentially offset with respect to one another.

In another embodiment, the openings comprise holes rather than slots. The holes are arranged in rows along at least a portion of the length of the flexible region. Preferably, the holes in adjacent rows are offset from each other along the length of the rows.

The hollow inner member receives suction at its proximal end to cause tissue fragments cut by the implement (e.g., a blade) to be transported away from the surgical site through the tube while the instrument remains in situ for further cutting.

Whether the outer tube is straight or curved, the flexible region accommodates itself to axial deviations in the outer member. As a result, deviations (actually minor bends in the outer tube that can occur during the rigors of surgery) which may otherwise cause the inner member to bind during rotation or the cutting implement to periodically pull away from the edges of the outer member openings as the inner member rotates, have little or no effect on the cutting efficiency of the instrument. The flexible region also maintains the close sliding contact as the cutting implement becomes worn.

The flexible region is fabricated integrally with a portion of the proximal end of the inner member from a continuous tube of thin material, and the wall thickness of the unrelieved portions of the flexible region is the same as that of the remainder of the tube. This simplifies manufacture by eliminating the need for assembling the flexible region separately and subsequently securing it to the remainder of the inner member. In one embodiment, the slots are formed by a wire EDM (electric discharge machining) process.

In another aspect of the invention, a region of the inner member is weakened with respect to the remainder of the member to cause the region to break if the force applied to the inner member exceeds a predetermined threshold.

Preferred embodiments include the following features.

The threshold is selected to be less than a maximum desired force to be applied to the cutting implement. As a result, the possibility of fracturing the cutting implement by the application of excessive force (e.g., torque) and the associated danger of slivers of the fractured cutting implement being ejected from the instrument into the surgical site is greatly reduced. The region is disposed sufficiently proximally of the tissue-cutting opening in the outer member so that if the region breaks, the broken portion of the inner member is captured within the inner member and does not escape through the opening. This significantly enhances the safety of the instrument.

The weakened region of the inner member preferably comprises the integral flexible region discussed in detail above. The instrument is preferably curved, but it may be straight instead.

In yet another aspect, pliable material is disposed in the openings of the flexible region. The pliable material impedes tissue fragments from becoming caught on the edges of the openings as the fragments pass through the inner member, thereby significantly reducing the risk of clogging. In addition, the pliable material decreases the axial compressibility of the inner member to maintain the cutting blade in proper alignment with the tissue opening in the outer member.

Preferred embodiments include the following features.

The pliable material is substantially coextensive with both the interior surface of the inner member (to provide a smooth inner surface for easy tissue passage) and the exterior surface of the inner member (so as not to interfere with the motion of the inner member within the outer member). The pliable material is a polymer such as silicone rubber.

The pliable material is applied in the openings over a mandrel that has been temporarily inserted into the inner member. The mandrel helps ensure that the pliable material is coextensive with the interior surface. Excess material that projects from the openings is then removed. The pliable material may be applied by injection molding.

Other features and advantages of the invention may be apparent from the following detailed description, and from the claims.

DESCRIPTION OF THE PREFERRED EMBODIMENTS

We first briefly describe the drawings.

FIG. 1 is a perspective view of a curved arthroscopic surgical instrument according to the invention.

FIG. 2 shows the instrument of FIG. 1 with the outer tube cross-sectioned to reveal the inner tube.

FIG. 3 is an enlarged view of the distal region of the inner tube of FIG. 2.

FIG. 4 shows a further enlargement of part of the flexible region of the tube of FIG. 3 encircled by dashed line 4.

FIGS. 5a and 5b are cross sections of the flexible region shown in FIG. 3 and taken along lines 5a—5a and 5b—5b.

Figure 6:
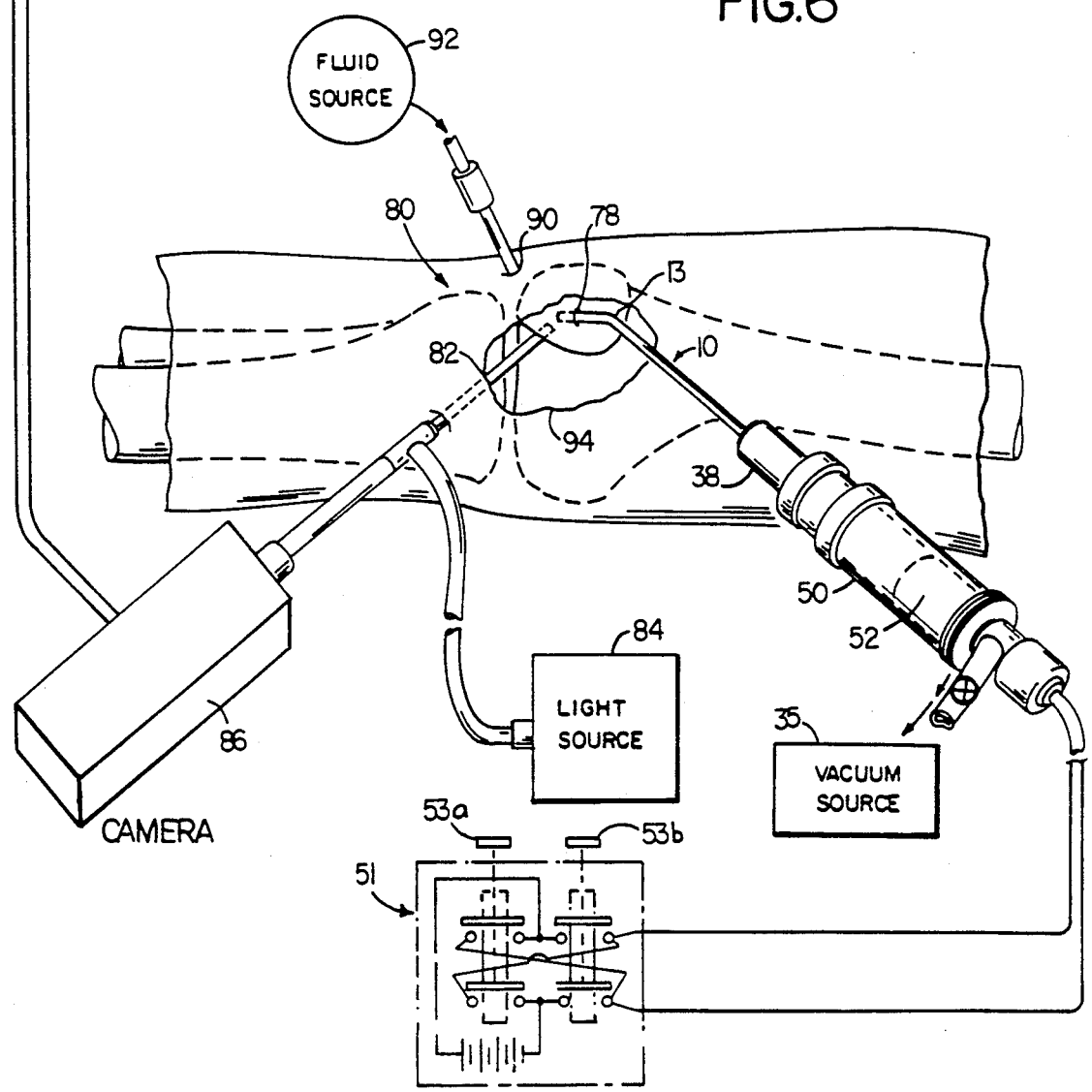

FIG. 6 illustrates the use of the surgical instrument of FIG. 1 during a surgical procedure.

FIGS. 7a and 7b illustrate another feature of the invention.

FIG. 8 shows an alternative embodiment of the invention.

Figure 9:
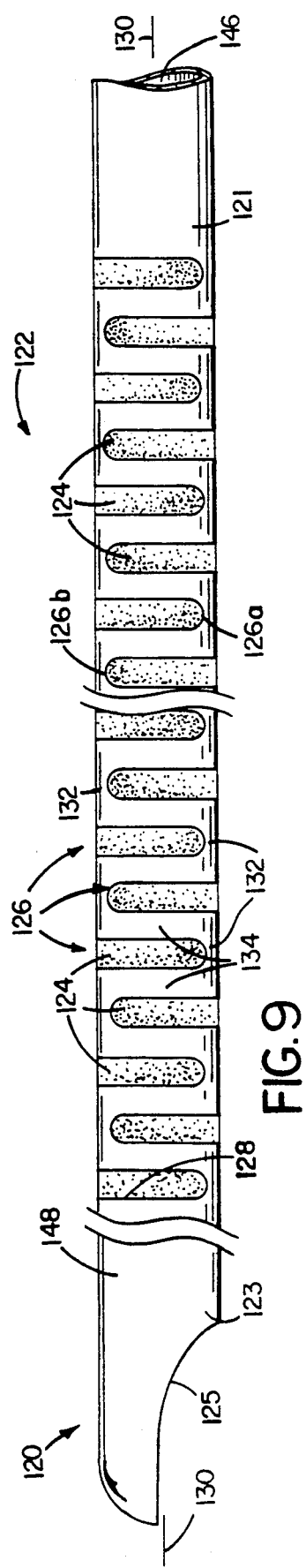

FIG. 9 illustrates another embodiment of the invention in which pliable material is disposed in the openings of the inner tube.

Figure 10:
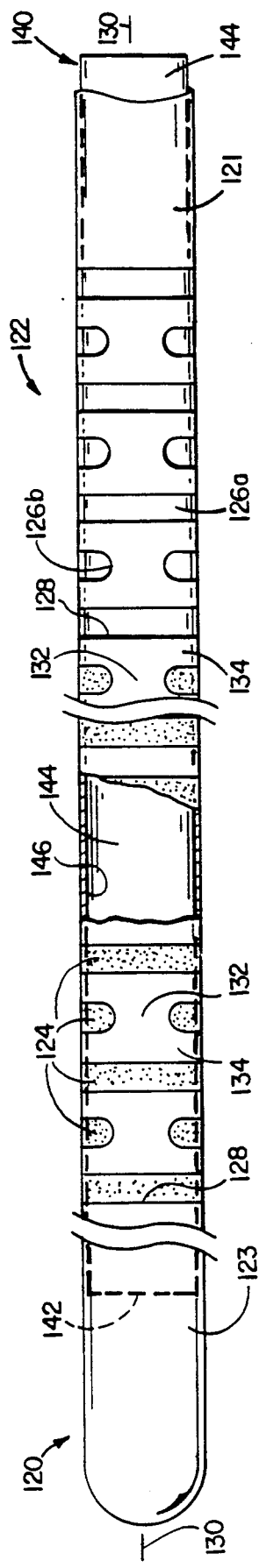
Figure 11:
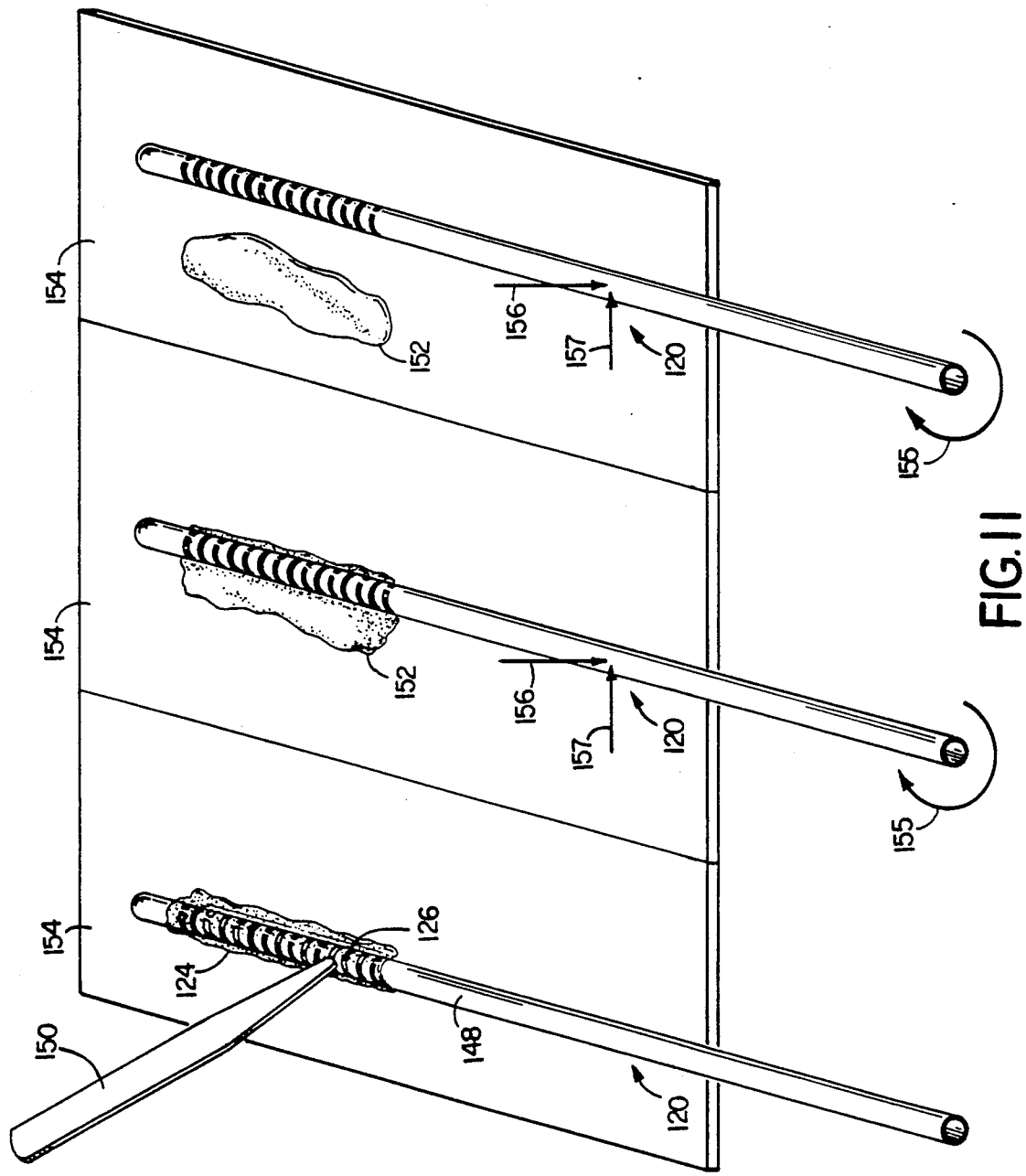

FIGS. 10 and 11 show steps in the process of applying the pliable material.

Figure 12:
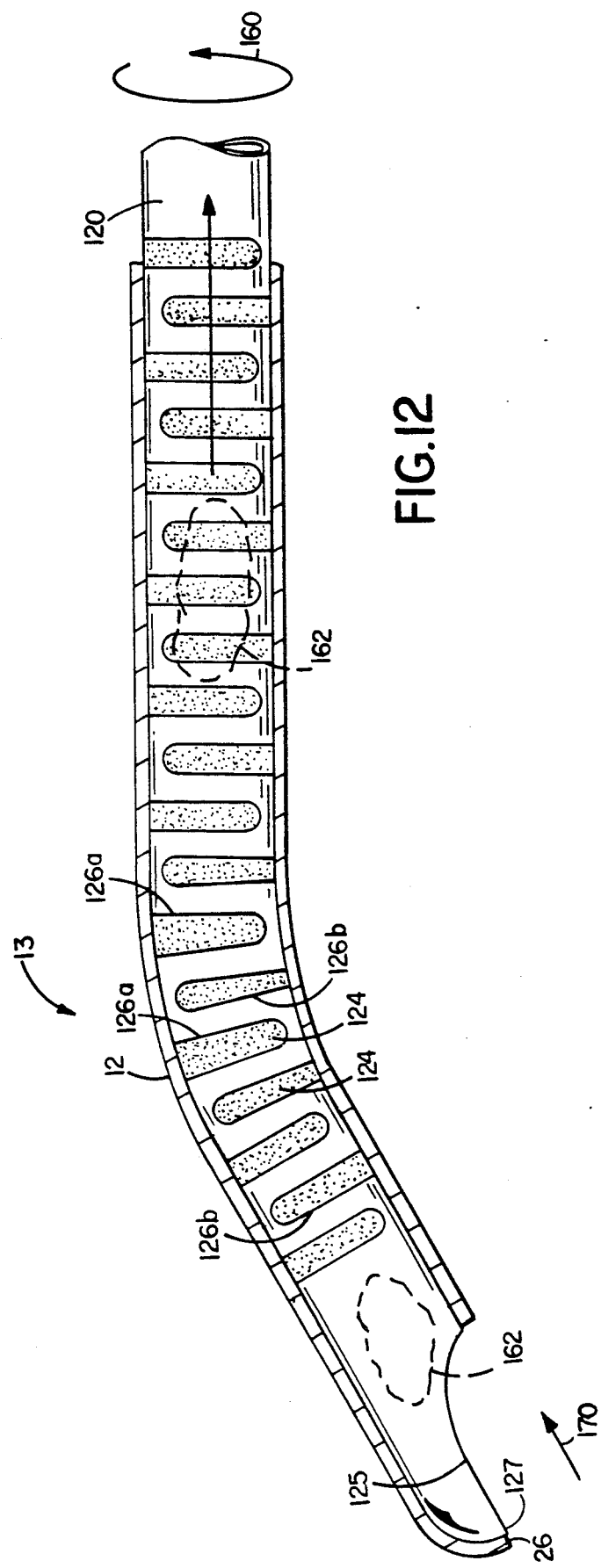

FIG. 12 is useful in understanding advantages that the pliable material provides.

STRUCTURE AND OPERATION

Referring to FIGS. 1 and 2, surgical instrument 10 suitable for, e.g., closed, arthroscopic surgery on the knee, includes a rigid, stationary outer tube 12 within which is disposed a rotating inner tube 14. A region 13 of outer tube 12 is curved to enable instrument 10 to operate on surgical areas that are difficult to reach with a straight instrument. The proximal region 17 and the distal region 28 of inner tube 14 are rigid and are connected by a flexible region 16 that accepts the curvature 13 imposed by outer tube 12 while transmitting torsion (or other forces) applied to proximal region 17 to distal region 28. Region 16 is made flexible by the selective removal of portions of material (represented by lines 18 in FIG. 2) from the walls 20 (FIG. 3) of inner tube 12. That is, tube 14 is relieved in flexible region 16.

Openings 22, 24 are provided at the distal ends 26, 28 of tubes 12, 14, respectively, which are periodically aligned as inner tube 14 rotates for admitting tissue to be severed into instrument 10. The edges 30 of inner tube opening 22 are sharp and cooperate with sharpened edges 32 of the opening 24 in outer tube 12 as tube 14 rotates to sever tissue caught between edges 30, 32. The severed tissue is removed via a central aperture 34 in inner tube 14.

The proximal end 36 of tube 12 and proximal end 17 of tube 14 are received by a base 38. Outer tube 16 is rigidly mounted to base 38 at a sealed joint 40, while inner tube 14 is secured to a drive shaft 42 that rotates within base 38. Drive shaft 42 is retained within base 38 by a pliable fitting 44. The proximal end 46 of drive shaft 42 fits into a handpiece 50 (FIG. 6), which includes a motor 52 for rotating drive shaft 42 and inner tube 14. One example of such a handpiece is described in U.S. Pat. No. 4,705,038, entitled "Surgical System for Powered Instruments", and assigned to the present assignee, which is incorporated by reference. Fitting 44 provides a fluid-tight seal when base 38 is inserted into handpiece 50.

Central aperture 34 terminates in a vacuum source opening 54 in drive shaft 42. Opening 54 is coupled to a vacuum source 55 (FIG. 6) during operation to remove severed tissue and irrigating fluid from the surgical site via aperture 34 in a manner described in detail below.

The material used for tubes 12, 14, depends on, among other things, the hardness of the tissue to be cut and whether instrument 10 is disposable or reusable. For a disposable instrument designed for general purpose arthroscopic surgery, tubes 12, 14 are fabricated from 304 stainless steel. Base 38 and its components (e.g., drive shaft 42) are plastic, but metal may be used as an alternative (e.g., for reusable instruments).

Referring also to FIGS. 3, 4, and 5a–5b, inner tube 14 is a thin-walled (e.g., about 0.010 inches) tube that is continuous between proximal end 17 through flexible region 16, and flexible region 16 is integrally formed with the proximal region 17 of inner tube 14. Flexible region 16 is relieved by forming a series of curved (i.e., circumferential) slots 60, 62 in the walls 20 of inner tube 14. The wall thickness of the unrelieved portions of flexible region 16 equal that of proximal region 17. Slots 60, 62 are generally perpendicular to the longitudinal axis 64 of inner tube 14 and are arranged in a symmetrical pattern along the length $L_1$ of flexible region 16 to ensure that region 16 is uniformly flexible along length $L_1$ and that the flexibility does not deviate substantially as tube 14 rotates within tube 12. This minimizes the torsional stress imposed on the rotating inner tube 14, thereby increasing the operating lifetime of instrument 10.

Specifically, slots 60 are all disposed parallel to each other (vertically in FIG. 3) along length $L_1$, and each slot 60 is opposed by an identical vertical slot 60 in a plane that is perpendicular to the longitudinal axis 64 of inner tube 14. Slots 62 are interposed between each pair of vertical slots 60 and are rotated by 90 degrees about axis 64 with respect to slots 60 (i.e., into the page in FIG. 3). That is, slots 60, 62 are circumferentially offset with respect to one another. As with slots 60, slots 62 are all parallel to each other, and each slot 62 is opposed by an identical slot 62 in a plane that is perpendicular to axis 64.

The dimensions of slots 60, 62 (i.e., their width $W_1$ and depth D), and the spacing S between adjacent, perpendicular slots 60, 62 are determined by the degree of flexibility desired. In this example, the width $W_1$ of each slot 60, 62 equals the thickness of inner tube wall 20 (e.g., 0.010 inches), as does the spacing S between adjacent, perpendicular slots 60, 62 (and thus the spacing between adjacent parallel slots, such as slots 60, is 0.020 inches).

A pair of opposing tabs 68 of limited circumferential extent remain between opposing slots 60 and are likewise disposed in a plane that is perpendicular to axis 64. A similar pair of opposing tabs 69 are located between each pair of opposing slots 62. Because of the orthogonal nature of slots 60, 62, tabs 68 are disposed at right angles with respect to tabs 69.

The depth D of slots 60, 62 is also a function of the desired torsional strength of flexible region 16. If depth D is too large, tabs 68, 69 will be too thin (i.e., their radial extent will be too small) to efficiently transmit torque applied by the motor to the rotating cutting edges 30 of inner tube 14. In this example, depth D is selected so that the circumferential extents (i.e., the widths) $W_2$ of tabs 68, 69 are equal and are approximately two wall thicknesses (i.e., 0.020 inches).

The arrangement of slots 60, 62 provides a series of rings 70 of material interconnected by pairs of tabs 68, 69 along the length $L_1$ of flexible region 16. Each ring 70 is interconnected with one of its immediately adjacent rings 70 by a pair of tabs 68, and is interconnected with the other one of its immediately adjacent rings 70 by a pair of tabs 69. The interconnected rings 70 form a series of essentially H-shaped leaf springs 72 along the length $L_1$ of flexible region 16, as shown in detail in FIG. 4. Because slots 60, 62 are arranged in a symmetrical pattern along region 16, so too are leaf springs 72. Specifically, pairs of vertically arranged (in FIG. 4) leaf springs 72 are interconnected by pairs of leaf springs 72 that are disposed into the page in FIG. 4. It is this symmetrical arrangement of interconnected, integrally formed leaf springs 72 that provides region 16 with both uniform flexibility and torsional stiffness, as explained in detail below.

Note that this arrangement provides several paths of material that are continuous between proximal region 17 and distal region 28 without traversing the circumference of inner tube 14. Two of these paths are shown in FIG. 3. One path includes the upper halves of each "H" of the interconnected leaf springs, and the other includes the lower halves of the H's of the interconnected leaf springs.

The length $L_1$ of flexible region 16 (e.g., 1 inch) is a function of the length of the curved region 13 in outer tube 12, and the spacing, $L_2$ (e.g., 0.5 inches), between the tip of inner tube 14 and the distal end of flexible region 16 depends both on the length of instrument 10 and the relative position of curved region 13 with respect to the tip of outer tube 12. These dimensions should be selected so that flexible region 16 spans the entire length of curved region 13, with the proximal and distal ends of flexible region 16 being disposed in the straight regions 15 (FIG. 2) of outer tube 12 that are disposed on either side of curved region 13. This allows flexible region 16 to make the transition between straight regions 15 through curved region 13 smoothly, thereby reducing the stress imposed by the curvature on the walls 20 of inner member 14.

Slots 60, 62 are formed by any suitable method, for example, by wire EDM (electric discharge machining) using 0.010 inch diameter wire. During the EDM process, inner tube 14 is held in place and an electrically charged wire is brought into contact with the outer surfaces of walls 20 to form each slot. The wire is oriented with respect to axis 64 so that the slots will have the desired orientation with respect to axis 64 (such as 90 degrees as shown in FIG. 3). The slots are formed in succession by stepping the wire along $L_1$, and all similarly oriented slots are formed before forming the remaining slots. For example, slots 62 disposed in the upper surface of tube 14 in FIG. 3 are formed by lowering the EDM wire against tube 14 from above. Then, the wire is applied from below to form slots 62 disposed in the lower surface of tube 14. Only then is tube 14 rotated so that slots 60 can be formed. The EDM wire is applied first from above to form half of slots 60, and when this is completed the wire is applied from below to form the remaining slots. Changing the position of tube 14 only once during the EDM process reduces the possibility of misalignment of slots 60, 62. The wire EDM process allows the flexible regions 16 of several inner tubes 14 to be formed at once (by arranging tubes 14 side by side so that the wire simultaneously acts on all of the tubes).

Alternatively, slots 60, 62 may be sawed into tube 14. Whatever method is used, slots 60, 62 should be fabricated in such a way so that their ends 76 are rounded rather than sharp. This inhibits the tendency of tabs 68, 69 to crack.

The distal end 28 of tube 14 is either integral with the remainder of tube 14 or is a separate steel piece rigidly secured (such as by low-carbon welding, soldering, or brazing) to tube 14 approximately 0.100 inches distally of flexible region 16.

Outer tube 12 has an inner diameter that is slightly larger than the outer diameter of inner tube 14. If the spacing between the tubes is too small, inner tube 14 will bind while rotating. The outer diameter of tube 14 is 0.135 inches, and tube 12 has an inner diameter of about 0.138 inches, which narrows slightly near the tip of distal end 26 to provide a tight bearing surface for distal end 28 of inner tube 14. This serves to urge rotating edges 30 into close contact with stationary edges 32 of outer tube 12 and improve cutting efficiency. The resiliency provided by flexible region 16 also urges the rotating distal end 28 of inner tube toward the walls of outer tube 12, thereby assisting in providing the close contact between edges 30, 32.

Referring also to FIG. 6, in operation, surgical instrument is inserted onto the distal end of a handpiece 50 and is introduced as shown through a puncture wound 78 into the knee joint 80, below the patella. Light is projected into the joint via a second puncture 82 using a fiber optic light source 84, and a visual image of the surgical site is returned through a separate optical path to a television camera 86. The image is delivered by camera 86 onto a television screen 88 for viewing by the surgeon. (Alternatively, the surgeon can view the image using an eyepiece, or the image can be recorded.)

Inner tube 14 is rotated by activating motor 51, which receives operating potential and current from power supply 51. The surgeon controls rotational speed and direction (either unidirectional or oscillatory) using foot switches 53a, 53b, which control the magnitude and polarity of operating potential and current provided by power supply 51 to motor 50. Motor 50 is capable of rotating inner tube over a wide range of speeds, e.g., between about 100 rpm and 5000 rpm, and can deliver a torque of up to 25 oz. inches.

Different types of surgical instruments such as instrument 10 have rotational and torsional limits. To prevent the surgeon from inadvertently operating instrument 10 at dangerously high speeds and torques, instrument 10 identifies to sensors in handpiece 50 what type of instrument it is, and the speed of and torsion applied by motor 50 is controlled so that these limits are not exceeded. (This control technique is described in the aforementioned U.S. Pat. No. 4,705,038, which is incorporated by reference.)

The rotation of motor 50 and the torsion that it provides are efficiently delivered to the cutting implement (i.e., rotating edges 30) by flexible region 16. Although region 16 is sufficiently flexible to accept curvature 13, it has a high degree of torsional stiffness and thus provides good torque response. That is, torsion applied by motor 50 is transmitted to distal end 28 substantially immediately when inner tube is rotated from its rest position, without requiring any significant "preloading" of flexible region 16 prior to passing the torque to distal end 28. Also, flexible region 16 does not expand in diameter by any significant amount as it rotates and applies torque to distal end 28, reducing the possibility that tube 14 will bind within outer tube 12 during rotation.

The torsional stiffness is in part a function of the shape of tabs 68, 69. If the width ($W_2$) of tabs 68, 69 is too narrow or the spacing between adjacent slots 60 or 62 too large, tabs 68, 69 become rather elongated, thereby reducing their strength. This would allow flexible region 16 to twist about tabs 68, 69 as torsion is applied, thereby reducing the torsional stiffness of tube 14.

During the surgical procedure, the body joint is inflated with fluid introduced through a third puncture wound 90 from a fluid source 92. The fluid irrigates the site and renders the synovial tissue 94 mobile so that it floats and can be displaced (similar to the movement of seaweed in water). The surgeon progressively cuts away the synovial tissue by moving instrument 10 from side to side and in the axial direction (while viewing television screen 88).

Tissue fragments cut by instrument 10 are withdrawn from the surgical site along with irrigation fluid via aperture 34 (FIG. 2) in response to suction applied by vacuum source 55. Note that as flexible region 16 rotates within the curved region 13 of outer tube, the width of each slot 60 or 62 at the periphery of tube wall 20 progressively increases and decreases incrementally with respect to the normal width $W_1$. This is because flexible region 16 tends to stretch at the apex of curve 13 (i.e., the upper part of curve 13 in FIG. 2) and compress at the base of the curve. This alternating widening and constricting as tube 14 rotates may generate turbulence in the fluid being withdrawn through aperture 34, thereby assisting in the transport of tissue fragments through the chamber and out of instrument 10. The exposure of aperture 34 to the interior walls of outer tube 12 through slots 60, 62 has not been found to allow tissue fragments to become caught in the slots and cause blockage, perhaps due to the small width of the slots and the continual rotation of tube 14. Fluid likewise has not been found to seep between tubes 12, 14 via slots 60, 62 in amounts that interfere with the operation of instrument 10.

If during the procedure the surgeon wishes to cut tissue from another region of the synovial tissue, he may do so simply by rotating and pivoting handpiece 50. The curvature of instrument 10 allows the cutting tip to be manipulated into regions of the joint that cannot be reached by a straight instrument inserted through the same puncture 78. Thus, additional punctures do not need to be made to manipulate curved surgical instrument 10 into other areas of the joint. This reduces patient discomfort, as well as the chances for infection and other deleterious consequences of the surgery.

Other embodiments are within the scope of the following claims.

Various arrangements of slots 60, 62 can be employed. The width and depth of the slots, their spacing, and indeed the configuration of the slots themselves can be varied to provide different degrees of flexibility and torsional stiffness. For example, the ratio of slot width to the width of tabs 68, 69 between the slots (which is 1:2 in the embodiment described above) could be increased, to reduce flexibility, or lowered, which would cause region 16 to be more flexible (but less torsionally stiff). Also, the spacing between adjacent slots 60, 62 (i.e., the width of rings 70) may be changed to provide greater or fewer slots per inch. Note that increasing this spacing (which reduces the fabrication costs) carries the tradeoff of reduced flexibility.

The flexibility of region 16 must also take into account the stresses imposed by the curvature (e.g., 10 degrees) of outer tube 12. If the stress exerted exceeds the yield strength of the material of inner tube 14 in flexible region, the material will fail. But care should be taken that the stress also does not exceed the fatigue limit of the material, in order to ensure a reasonable operating lifetime.

Adjacent slots 60, 62 need not be oriented perpendicularly around axis 64, nor must the width of tabs 68, 69 be equal. For example, slots 60, 62 may be configured so that tabs 68, 69 are arranged in a helical pattern along flexible region 16.

There also need not be only two opposing slots in each set. For example, each set of slots (e.g., slots 60) can include three slots arranged around the circumference of wall 20. The slots may be equally spaced to provide uniform flexibility as inner tube 14 rotates, and thus three slots would oppose each other at an angle of approximately 120 degrees. The tabs between adjacent slots 60, 62 would be oriented at 60 degrees relative to each other rather than at 90 degrees as are tabs 68, 69.

Referring to FIGS. 7a and 7b, the usefulness of integral flexible region 16 is not limited to curved instruments. Instrument 110 includes a straight outer tube 112 within which inner tube 114 having integral flexible region 16 rotates in the same manner as discussed above. Flexible region 16 accommodates itself to deviations by outer tube 112 from its longitudinal axis 113 (caused, e.g., by the surgeon wedging the instrument between bones to cut difficult to reach tissue). As a result, inner tube 114 is less likely to bind as it rotates within the bent outer tube 112, and the cutting edges of inner tube 114 are maintained in close sliding contact with the cutting edges of outer tube 112. Flexible region 16 functions in a similar manner to compensate for wear in the cutting edges.

The reduction in the strength of flexible region 16 that is inherent in removing material from walls 20 can be used as a so-called "controlled break" in either a straight instrument or a curved instrument to provide a built-in torque limiter. That is, flexible region 16 can be relieved to a degree selected to cause it to break if the applied torsional force exceeds a predetermined limit which is selected to be slightly lower than the maximum specified torque for the cutting implement on the inner tube. Thus, flexible region 16 acts as a "fuse" to cause the instrument to fail before the torque limit of the cutting implement on the inner tube is exceeded. This prevents, e.g., a cutting blade from fracturing and fragments of the blade being expelled into the surgical site because its maximum specified torque has been exceeded. Instead, the inner tube itself breaks proximally of the opening in the outer tube, and the broken distal end of the inner tube is captured within the outer tube. If the instrument is straight rather than curved, the length of flexible region 16 need only be sufficient to give the desired torque limit.

Referring to FIG. 8, material need not be removed from inner tube 14 in the shape of slots. For example, flexible region 16' includes alternating rows of holes 100, 102 drilled through the walls of inner tube 14. Each hole is 0.050 inches in diameter, and the holes in each row are separated by 0.120 inches. The axes of adjacent rows 100, 102 are also spaced by 0.050 inches, and rows 100, 102 are offset along longitudinal axis 64 of tube 14 by about 0.050 inches. Flexible region 16' is tapered (at about 5 degrees) with respect to the remainder of tube 14 to reduce its outer diameter to approximately 0.128 inches. This reduces the possibility of binding within curved region 13 of outer tube 12 as inner tube 14 rotates.

Many types of arthroscopic cutting implements can be used as alternatives to the implement shown in the figures. Examples of such cutting implements are shavers, cutters, abraders, and forceps, as described in the aforementioned U.S. Pat. Nos. 4,203,444, 4,274,414, 4,522,206, 4,662,371, 4,834,729, and 4,842,578, all of which are incorporated by reference. The cutting implement may also be a drill bit.

The inner tube can be of the type that is moved translationally (such as reciprocally) along the longitudinal axis of the outer tube (either instead of or in addition to being rotated). Flexible region 16 (or 16') also has a high degree of translational stiffness, and thus efficiently transmits the applied axial force to the cutting implement. The surgical instrument need not be a powered instrument.

Other materials may also be employed. For example, the inner tube may be plastic rather than metal, so long as the plastic is durable enough to withstand the stresses imposed during operation. The slots would be formed during the plastic molding process.

The flexible inner tube according to the invention may also be used in surgical instruments other than arthroscopic instruments.

Referring to FIGS. 9-12, inner tube 120 includes a flexible region 122 between rigid proximal and distal ends 121, 123, respectively, that has pliable silicone rubber 124 (such as RTV 732 available from Dow Corning Corporation) disposed in each slot 126 (slots 126 are shown significantly enlarged in FIGS. 9-12 for clarity). Silicone rubber 124 fills each slot 126 and helps avoid clogging by reducing the tendency of tissue fragments to become caught on the edges 128 of slots 126 as the fragments pass through inner tube 120. Although silicone rubber 124 is flexible, it is less compressible than empty space, and thus pliable material 124 serves to reduce the compressibility of flexible region 122 along the longitudinal axis 130 of inner tube 120.

As shown in FIGS. 9 and 10, adjacent slots 126a, 126b extend into inner tube 120 in opposite directions. (Tube 120 is shown from one side in FIG. 9 and from above in FIG. 10.) Slots 126a are cut into tube 120 from above, and slots 126b are formed from below. Slots 126 are each approximately 0.020 inches wide, and adjacent slots 126a, 126b are spaced by about 0.020 inches. Each slot 126a, 126b defines an arc of approximately 276 degrees, leaving an 89 degree arcuate tab 132 between the ends of the slot. Tabs 132 extend axially and are interconnected by rings 134 disposed between the adjacent slots. Flexible region 122 is slightly over one inch long and includes twenty-eight slots 126 (fourteen each of slots 126a and slots 126b).

After slots 126 have been formed, inner tube 120 is cleaned using any suitable degreasing solvent so that silicone rubber 124 will easily and durably adhere to the surfaces of the tube (i.e., the walls of slots 126). A mandrel 140 is then temporarily inserted into inner tube 120 via proximal end 121. Mandrel 140 serves to support silicone rubber 124 within slots 126 while the pliable material is being applied. Silicone rubber 124 is shown in less than all of slots 126 for purposes of illustration.

The distal end 142 of mandrel 140 extends distally of slots 126 into tube distal end 123. The outer diameter of mandrel 140 is selected so that the exterior surface 144 of mandrel snugly engages the interior surface 146 of inner tube 120. This helps ensure that pliable material 124 will be coextensive with interior surface 146, thereby rendering interior surface 146 smooth throughout flexible region 122.

Referring to FIG. 11, silicone rubber 124 can be applied manually by working it into slots 126 with a tool 150. Excess silicone rubber 152 that projects from slots 126 above the exterior surface 148 of inner tube 120 is removed by spinning tube 120 in the direction of arrow 155 while pressing it against a paper sheet 154 (shown by arrow 156). This causes excess 152 to be transferred to sheet 154 as tube 120 is rolled 157. Silicone rubber 124 is then cured at room temperature for about twenty-four hours. Alternatively, tube 120 can be baked at approximately 200° F. for about one-half hour to cure silicone rubber 124.

After silicone rubber 124 cures, the application process is repeated, if necessary, with a second coat of silicone rubber to fill in any valleys within slots 126. The removal of excess material restricts silicone rubber 124 to be coextensive with exterior surface 148 so that silicone rubber 124 does not interfere with the movement of tube 120 within an outer tube (such as tube 12, FIG. 1).

Referring to FIG. 12, during operation, the rotation of inner tube 120 within a curved outer tube 12 (such as in the direction of arrow 160) causes the slots 126a, 126b in curved region 13 to alternately expand and compress. That is, the slots open slightly as they approach the outer portion of curved region 13 (slots 126a are shown in this configuration) and then close partially as they rotate further and approach the inner portion of curved region 13 (as shown by slots 126b). In the absence of silicone rubber 124 in slots 126, this opening and closing motion may tend to cause tissue fragments 162 cut by blade 125 to become caught on edges 128 (FIG. 10) of slots 126. Silicone rubber 124 prevents tissue fragments from extending into slots 126 and smooths out the interior surface 146 of inner tube 120, thereby allowing tissue fragments 162 to pass through flexible region 122 easily, without snagging on edges 128. The risk of clogging is thus significantly reduced.

The opening and closing motion of slots 126 also may tend to cause flexible region 122 to compress along its longitudinal axis 130 as it rotates, which would have the undesirable effect of causing the distal tip 127 of tube 120 to slide axially (in the direction of arrow 170) away from the distal tip 26 of outer tube 12, leaving a gap between the tips. Silicone rubber 124 is less compressible than air, and although silicone rubber 124 pliably expands and compresses within slots 126 as inner tube 120 rotates, it restricts the extent of the slot expansion and compression. As a result, the axial compressibility of inner tube 120 is reduced, substantially eliminating the creation of a gap between distal tips 26, 127. The cutting edges of inner and outer tubes 12, 120 (and the openings that they define) are maintained in proper alignment for efficient cutting.

Other pliable material may be used in place of silicone rubber. The material should be flexible and can be an elastomer, a polymer, etc. Silicone rubber 124 can be applied by a machine rather than manually. For example, injection molding can be employed. One material that can be injection molded is Kraton ® (an injection-moldable rubber), available from Shell Chemical Company.

We claim:

1. A surgical instrument that is constructed for insertion into a body cavity for cutting tissue therein, comprising
a rigid outer member having an opening in a distal region thereof for admitting said tissue, and
a hollow inner member having rigid proximal and distal ends disposed within said outer member for transmitting force applied to said proximal end to move a cutting implement disposed at said distal end, said cutting implement being constructed to cut said tissue that is exposed to said implement through said opening,
a region of said inner member disposed between said proximal and distal ends being relieved so that, when straight, said region includes a plurality of openings disposed in walls thereof to render said region relatively flexible, said walls of said region having a thickness that is substantially the same as a thickness of walls of at least a portion of said proximal end disposed adjacent to said region, said region having sufficient stiffness to transmit said applied force to said cutting implement an cause it to cut said tissue.

2. The instrument of claim 1 wherein said outer member includes a curved region disposed proximally of said distal region, said flexible region of said inner member being disposed within at least a portion of said curved region of said outer member.

3. The instrument of claim 2 wherein said curved region is bounded on at least one side by a straight region of said outer member, a portion of said flexible region being disposed within at least a portion of said straight region.

4. The instrument of claim 3 wherein said curved region is bounded on two sides by straight regions, said flexible region being sufficiently long to span said curved region and be disposed in at least a portion of each said straight region.

5. The instrument of claim 1 or 2 wherein said openings are disposed in a symmetrical pattern.

6. The instrument of claim 1 or 2 wherein said openings comprise a plurality of slots each of which extends over a section of the circumference of said inner member, said slots being disposed along at least a portion of the length of said flexible region.

7. The instrument of claim 6 wherein said slots are circumferentially offset with respect to one another.

8. The instrument of claim 6 wherein said slots are disposed in a succession of planes perpendicular to a longitudinal axis of said inner member and a set of said slots are disposed in each said plane, the slots in adjacent planes being offset circumferentially with respect to one another.

9. The instrument of claim 8 wherein said sets of

10. The instrument of claim 1 or 2 wherein said openings comprise generally round holes.

11. The instrument of claim 10 wherein said holes are arranged in a plurality of rows disposed along at least a portion of the length of said flexible region.

12. The instrument of claim 11 wherein said holes in adjacent rows are offset from each other along said length.

13. The instrument of claim 1 wherein said force is applied to rotate said inner member.

14. The instrument of claim 13 wherein said force is applied by a motor that applies a torque to said inner member, said flexible region being configured to transmit said applied torque to said cutting implement.

15. The instrument of claim 1 wherein said hollow inner member is adapted receive suction at its proximal end and to transport tissue fragments cut by said cutting implement away from a surgical site while the instrument remains in situ for further cutting.

16. The instrument of claim 1 wherein said cutting implement comprises a blade.

17. The instrument of claim 1 wherein a region of said outer member within which said flexible region is disposed is arranged generally along an axis and said force is applied to rotate said inner member, said flexible region being adapted to accommodate itself to deviations in said region of said outer member from said axis.

18. The instrument of claim 17 wherein said outer member includes a curved region, said flexible region of said inner member being disposed within at least a portion of said curved region.

19. A surgical instrument that is constructed for insertion into a body cavity for cutting tissue therein, comprising
a rigid outer member having an opening in a distal region thereof for admitting said tissue, and
a hollow inner member having rigid proximal and distal ends disposed within said outer member for transmitting force applied to said proximal end to move a cutting implement disposed at said distal end, said cutting implement being constructed to cut said tissue that is exposed to said implement through said opening,
a region of said inner member disposed between said proximal and distal ends being configured to be relatively flexible, said region and at least a portion of said proximal end that is disposed adjacent to said region comprising a single member.

20. The instrument of claim 19 wherein said outer member includes a curved region disposed proximally of said distal region, said flexible region of said inner member being disposed within at least a portion of said curved region of said outer member.

21. The instrument of claim 20 wherein said inner member is relieved to render it flexible in said region.

22. The instrument of claim 19 or 20 wherein said inner member is relieved to render it flexible in said integral region.

23. The instrument of claim 22 wherein said flexible region is relieved with a plurality of openings disposed in walls of said inner member.

24. The instrument of claim 23 wherein said holes comprise a plurality of circumferentially extending slots disposed in a succession of planes along at least a portion of a longitudinal axis of said inner member, a set of said slots being disposed in each said plane, the slots in adjacent planes being circumferentially offset with respect to one another.

25. The instrument of claim 23 wherein said openings comprise holes arranged in a plurality of rows disposed along at least a portion of the length of said flexible region, holes in adjacent rows being offset from each other along said length.

26. A surgical instrument that is constructed for insertion into a body cavity for cutting tissue therein, comprising
an outer member having an opening in a distal region thereof for admitting said tissue,
a movable cutting implement adapted to cut said tissue that is exposed to said implement through said opening, and
a hollow inner member disposed within said outer member for transmitting force applied to a proximal end of said inner member to move said cutting implement, a region of said inner member including a plurality of discrete openings disposed in walls thereof, said openings having a size selected to weaken said inner member with respect to the remainder of said inner member to cause said region to break if the force applied to said inner member exceeds a predetermined threshold, said region and at least a portion of said rigid proximal end disposed adjacent to said region comprising a unitary structure.

27. The instrument of claim 26 wherein said threshold is selected to be less than a maximum desired force to be applied to said cutting implement.

28. The instrument of claim 26 wherein said force is rotational force and said threshold is a torque threshold.

29. The instrument of claim 26 wherein said weakened region is disposed a predetermined distance proximally of said opening so that, if said region breaks, the portion of said inner member disposed distally of the break is captured within said outer member.

30. The instrument of claim 26 wherein said relieved, weakened region is integral with said proximal end of said inner member.

31. The instrument of claim 30 wherein said openings comprise circumferentially extending slots.

32. The instrument of claim 26 wherein said outer member includes a curved region, said weakened region of said inner member being disposed within at least a portion of said curved region.

33. A surgical instrument that is constructed for insertion into a body cavity for cutting tissue therein, comprising
an outer member having an opening in a distal region thereof for admitting said tissue,
a movable cutting implement adapted to cut said tissue that is exposed to said implement through said opening, and
a hollow inner member disposed within said outer member for transmitting force applied to a proximal end of said inner member to move said cutting implement,
a region of said inner member including a plurality of discrete openings disposed in walls thereof, said openings comprising generally round holes having a size selected to weaken said inner member with respect to the remainder of said inner member to cause said region to break if the force applied to said inner member exceeds a predetermined threshold, said region and at least a portion of said rigid proximal end disposed adjacent to said region comprising an integral, unitary structure.

34. A surgical instrument that is constructed for insertion into a joint space of a body for cutting tissue therein, comprising
a hollow member having rigid proximal and distal ends for transmitting force applied to said proximal end to move a cutting implement disposed at said distal end, said cutting implement being constructed to cut said tissue to which it is exposed,
a region of said member disposed between said proximal and distal ends having a plurality of openings disposed in walls thereof to render said region relatively flexible while providing said region with sufficient stiffness to transmit said applied force to said cutting implement and cause it to cut said tissue, said walls of said region having a thickness that is substantially the same as a thickness of walls of at least a portion of said proximal end disposed adjacent to said region, and
pliable material disposed in said openings.

35. The instrument of claim 34 further comprising a rigid outer member having an opening in a distal region thereof for admitting said tissue, said hollow member being disposed along an axis within said outer member so that said applied force causes said hollow member to move with respect to said outer member so that said cutting implement moves past said opening to cut said tissue exposed to said implement though said opening, said pliable material reducing axial compression of said hollow member during movement thereof.

36. The instrument of claim 35 wherein said outer member includes a curved region disposed proximally of said distal region, said flexible region of said hollow member being disposed within at least a portion of said curved region.

37. The instrument of claim 35 wherein said force is applied by a motor that applies a torque to said hollow member, said flexible region being configured to transmit said applied torque to said cutting implement.

38. The instrument of claim 34 wherein said pliable material comprises a polymeric material.

39. The instrument of claim 38 wherein said pliable material comprises silicone rubber.

40. A surgical instrument that is constructed for insertion into a joint space of a body for cutting tissue therein, comprising a hollow member having rigid proximal and distal ends for transmitting force applied to said proximal end to move a cutting implement disposed at said distal end, said cutting implement being constructed to cut said tissue to which it is exposed, a region of said member disposed between said proximal and distal ends having a plurality of openings disposed in walls thereof to render said region relatively flexible while providing said region with sufficient stiffness to transmit said applied force to said cutting implement and cause it to cut said tissue, said walls of said region having a thickness that is substantially the same as a thickness of walls of at least a portion of said proximal end disposed adjacent to said region, and pliable material disposed in said openings, wherein said openings define edges on an interior surface of said hollow member, said pliable material being disposed to be substantially coextensive with said interior surface at said edges.

41. The instrument of claim 40 wherein said hollow member is adapted to receive suction at its proximal end and to transport tissue fragments cut by said cutting implement away from a surgical site while the instrument remains in situ for further cutting, said pliable material being disposed to provide a substantially smooth surface for passage of said tissue fragments through said flexible region to reduce the tendency of said tissue fragments to become caught on said edges.

42. A surgical instrument that is constructed for insertion into a joint space of a body for cutting tissue therein, comprising a rigid outer member having an opening in a distal region thereof for admitting said tissue, a hollow member disposed along an axis within said outer member, said hollow member having rigid proximal and distal ends and being responsive to a force applied to said proximal end by moving with respect to said outer member to transmit said force to move a cutting implement disposed at said distal end past said opening, said cutting implement being constructed to cut said tissue to which it is exposed through said opening, a region of said hollow member disposed between said proximal and distal ends having a plurality of openings disposed in walls thereof to render said region relatively flexible while providing said region with sufficient stiffness to transmit said applied force to said cutting implement and cause it to cut said tissue, said walls of said region having a thickness that is substantially the same as a thickness of walls of at least a portion of said proximal end disposed adjacent to said region, and pliable material disposed in said openings, said pliable material reducing axial compression of said hollow member during movement thereof, said openings defining edges on an exterior surface of said hollow member, said pliable material being disposed to be substantially coextensive with said exterior surface at said edges.

43. A surgical instrument that is constructed for insertion into a body cavity for cutting tissue therein, comprising a rigid outer member having an opening in a distal region thereof for admitting said tissue, said outer member including a curved region disposed proximally of said distal region, a hollow inner member having rigid proximal and distal ends disposed within said outer member for transmitting force applied to said proximal end to move a cutting implement disposed at said distal end, said cutting implement being constructed to cut said tissue that is exposed to said implement through said opening, a region of said inner member disposed between said proximal and distal ends having a plurality of openings disposed in walls thereof to render said region relatively flexible while providing said region with sufficient stiffness to transmit said applied force to said cutting implement and cause it to cut said tissue, said flexible region being disposed within at least a portion of said curved region, said region having an inner diameter that is substantially the same as an inner diameter of at least a portion of said hollow inner member disposed adjacent to said member, and pliable material disposed in said openings.

44. A surgical instrument that is constructed for insertion into a body cavity for cutting tissue therein, comprising a rigid outer member having an opening in a distal region thereof for admitting said tissue, and a hollow inner member having rigid proximal and distal ends disposed within said outer member for transmitting force applied to said proximal end to move a cutting implement disposed at said distal end, said cutting implement being constructed to cut said tissue that is exposed to said implement through said opening, a region of said inner member disposed between said proximal and distal ends being relieved with a plurality of axially and circumferentially spaced, discrete openings to render said region relatively flexible while providing said region with sufficient stiffness to transmit said applied force to said cutting implement and cause it to cut said tissue, said region having an inner diameter that is substantially the same as an inner diameter of at least a portion of said hollow inner member disposed adjacent to said member.

45. The instrument of claim 44 further comprising pliable material disposed in said openings.

46. The instrument of claim 1, 19, 26, 34, 43, or 44 wherein said body cavity is a joint space.

47. A surgical instrument that is constructed for insertion into a joint space of a body for cutting tissue therein, comprising a hollow member having rigid proximal and distal ends for transmitting force applied to said proximal end to move a cutting implement disposed at said distal end, said cutting implement being constructed to cut said tissue to which it is exposed, a region of said member disposed between said proximal and distal ends having a plurality of openings disposed in walls thereof to render said region relatively flexible while providing said region with sufficient stiffness to transmit said applied force to said cutting implement and cause it to cut said tissue, said walls of said region having a thickness that is substantially the same as a thickness of walls of at least a portion of said proximal end disposed adjacent to said region, and pliable material disposed on said inner member to cover at least one of said openings. slots are uniformly spaced along said axis.

* * * * *

UNITED STATES PATENT AND TRADEMARK OFFICE
CERTIFICATE OF CORRECTION

PATENT NO. : 5,322,505
DATED : June 21, 1994
INVENTOR(S) : Kenneth W. Krause, et. al.

It is certified that error appears in the above-indentified patent and that said Letters Patent is hereby corrected as shown below:

On the cover page of the patent delete:

"[30]     Foreign Application Priority Data

Oct 11, 1991 [DE] Fed. Rep. of Germany ...... 4133696
   Mar. 10, 1992 [DE] Fed. Rep. of Germany ...... 4207557"

Col. 12, claim 9, line 49 after "sets of" insert --slots are uniformly spaced along said axis.--

Col. 13, claim 22, line 37-39, delete in its entirety and replace with:
   --22. A surgical instrument that is constructed for insertion into a body cavity for cutting tissue therein, comprising
   a rigid outer member having an opening in a distal region thereof for admitting said tissue, and
   a hollow inner member having rigid proximal and distal ends disposed within said outer member for transmitting force applied to said proximal end to move a cutting implement disposed at said distal end, said cutting implement being constructed to cut said tissue that is exposed to said implement through said opening,

UNITED STATES PATENT AND TRADEMARK OFFICE
CERTIFICATE OF CORRECTION

PATENT NO. : 5,322,505
DATED : June 21, 1994
INVENTOR(S) : Kenneth W. Krause, et. al.

It is certified that error appears in the above-indentified patent and that said Letters Patent is hereby corrected as shown below:

a region of said inner member disposed between said proximal and distal ends being configured to be relatively flexible, said region and at least a portion of said proximal end that is disposed adjacent to said region comprising a single member, said inner member being relieved to render it flexible in said region.--

Col.18, claim 47, lines 12-13, after "openings" delete -- slots are uniformly spaced along said axis--

Signed and Sealed this

Eleventh Day of October, 1994

Attest:

BRUCE LEHMAN

Attesting Officer

Commissioner of Patents and Trademarks